United States Patent [19]

Dyer

[11] Patent Number: 6,013,677
[45] Date of Patent: Jan. 11, 2000

[54] ANTIMICROBIAL NAIL COATING COMPOSITION

[75] Inventor: David L. Dyer, Cypress, Calif.

[73] Assignee: Woodward Laboratories, Inc., Los Alamitos, Calif.

[21] Appl. No.: 09/226,413

[22] Filed: Jan. 6, 1999

Related U.S. Application Data

[60] Division of application No. 09/006,811, Jan. 14, 1998, which is a continuation-in-part of application No. 08/993,464, Dec. 18, 1997, abandoned, which is a continuation-in-part of application No. 08/756,958, Dec. 3, 1996, Pat. No. 5,827,870.

[51] Int. Cl.[7] .............................. A01N 33/12; A01N 33/14
[52] U.S. Cl. ............................................... 514/643; 424/61
[58] Field of Search ................................ 514/643; 424/61

[56] References Cited

U.S. PATENT DOCUMENTS

| | | | |
|---|---|---|---|
| 2,577,773 | 3/1947 | Lambert | 252/152 |
| 2,765,257 | 10/1956 | Blackburn | 167/85 |
| 2,799,613 | 7/1957 | Blödorn | 167/30 |
| 3,419,006 | 12/1968 | King | 128/268 |
| 3,968,246 | 7/1976 | Merianos et al. | 424/330 |
| 4,203,872 | 4/1980 | Flanagan | 252/542 |
| 4,250,164 | 2/1981 | Bernstein | 424/61 |
| 4,278,665 | 7/1981 | VanCleave | 424/148 |
| 4,336,151 | 6/1982 | Like et al. | 252/106 |
| 4,721,724 | 1/1988 | Stettendorf et al. | 514/396 |
| 4,797,420 | 1/1989 | Bryant | 514/643 |
| 4,810,498 | 3/1989 | DiMeglio | 424/195.1 |
| 4,957,730 | 9/1990 | Bohn et al. | 424/61 |
| 5,045,039 | 9/1991 | Bay | 493/1 |
| 5,118,495 | 6/1992 | Nafziger et al. | 424/61 |
| 5,181,914 | 1/1993 | Zook | 604/307 |
| 5,284,833 | 2/1994 | McAnalley et al. | 514/23 |
| 5,346,692 | 9/1994 | Wohlrabet et al. | 424/61 |
| 5,362,422 | 11/1994 | Masters | 252/544 |
| 5,399,343 | 3/1995 | Smith, Jr. | 424/61 |
| 5,439,682 | 8/1995 | Wivell et al. | 424/401 |
| 5,487,776 | 1/1996 | Nimni | 106/18.35 |
| 5,516,509 | 5/1996 | Marr-Leisy et al. | 424/61 |

FOREIGN PATENT DOCUMENTS 2108840   5/1983   United Kingdom .

OTHER PUBLICATIONS

Derwent Publications, Ltd., AN 96–450913, JP 08225433 A, "Aqueous cosmetics for nails", Sep. 3, 1996, vol. 45, 1 page abstract.

Derwent Publications, Ltd., AN 88–128277, GB 2196978 A, "Nail strengthening compsn. contg. glyoxal –in standard nitrocellulose based nail lacquer", May 11, 1988, vol. 19, 1 page abstract.

Fisher, A.A., M.D., "Allantoin: A Non–Sensitizing Topical Medicament Therapeutic Effects of the Addiction of 5 Percent Allantoin to Vaseline®", 1981, 1–3.

Katz, N.D., D.P.M., "Tough as Nails . . . Fungoid® Tincture," Cutis, May 1992, (Podiatry Management, Aug. 1993 issue).

Sutton Laboratories, Inc., Fact Sheet on Allantoin, Jan. 1, 1992, 1–6.

Allantoin –Product Information Sheet, 2 pages.

Germaben® II–E –Product Information Sheet, 2 pages.

Shanksky, A., "Establishing Physical Parameters for Nail Lacquers", Drug Cosmet. Ind., 1978, 123 (5), 46–49.

Wilkinson, J.B. and Morre, R.J. (eds.), "Manicure Preparations", Harry's Cosmeticology, Seventh Edition, Chemical Publishing Company, Inc., New York, N.Y., Chapter 22, 1982, 369–393.

Primary Examiner—Frederick Krass
Attorney, Agent, or Firm—Woodcock Washburn Kurtz Mackiewicz & Norris LLP

[57] ABSTRACT

Antimicrobial nail coating compositions, and methods for treating and preventing microbial infections of the nail area, are provided. The antimicrobial nail coating compositions can be used to treat and/or prevent infections caused by microbes including bacteria, molds, spores, viruses and fungi, while providing a nail coating having acceptable handling and esthetic qualities. The compositions can include alcohol-containing solvents, and, as antimicrobial agents, quaternary amines or phenols.

7 Claims, No Drawings

ANTIMICROBIAL NAIL COATING COMPOSITION

This application is a division of U.S. application Ser. No. 09/006,811, filed Jan. 14, 1998, which is a continuation-in-part of U.S. application Ser. No. 08/993,464, filed Dec. 18, 1997 and now abandoned, which is a continuation-in-part of U.S. application Ser. No. 08/756,958, filed Dec. 3, 1996 and now U.S. Pat. No. 5,827,870.

FIELD OF THE INVENTION

The present invention relates to antimicrobial nail coating compositions, and to methods for preparing and using those compositions. In particular, the present invention relates to antimicrobial nail coating compositions useful in treating and preventing the spread of infections of the nail area caused by bacteria, fungi and other microbes.

BACKGROUND OF THE INVENTION

Nail coatings for cosmetic purposes, known variously as base coats, top coats, lacquers, varnishes, and enamels are the largest and most important group of manicure preparations. "The Nails", Chapter 22 in *Harry's Cosmeticology*, Wilkinson, J. B., and Moore, R. J., Eds., 7th Edition, pp 369–393. Chemical Publishing Company, Inc., New York, N.Y. 1982. Although nail coatings are generally collectively referred to as "nail polishes", such nomenclature is erroneous. Polishes contain fine abrasives that impart desirable characteristics, such as smoothness, based on friction created by buffing. Nail coatings, on the other hand, impart similar characteristics without friction due to components contained therein.

It is preferable that nail coatings be easily applied, dry rapidly and uniformly, convey a high luster upon drying, and be substantially non-toxic. The application process can be messy and time consuming. Thus, it is also desirable that such coatings be durable to avoid frequent applications. Other desirable characteristics of nail coatings include smooth and even flow on application and uniform drying without adverse surface artifacts.

The vast majority of nail coating systems currently in use contain either toluene or formaldehyde, or a combination of toluene and/or formaldehyde with aryl resins. Toluene and formaldehyde have an extremely unpleasant odor, are toxic by ingestion or absorption through the skin, and can easily sensitize the skin, leading to hypersensitivity. Aldehydes are also immunoreactive agents, which can promote inflammation and cause desiccation of vital tissue. Furthermore, toluene and formaldehyde have been recently recognized as carcinogens by CAL OSHA and other health and safety regulatory agencies (See, e.g., United States Department of Labor OSHA Standard Subpart Z 1910.1048). Thus, it is desirable to minimize or eliminate toluene and aldehydes, particularly formaldehyde, from nail coating formulations.

In part due to the inherent high volatility and enhanced evaporation coefficients of nail coatings, moisture and organic contaminants such as bacteria, molds, spores, viruses and fungi can become trapped on the nail surface and between the nail coating and the nail plate, resulting in polymicrobial infections of the nail plate and brittle, unsightly, disfigured nails. Onychomycosis is just one example of the myriad of microbial etiologies of nail disfigurement. Treatment of polymicrobial infections of the nail plate can require expensive, prolonged medical therapy, which is not always innocuous and can even be toxic. Moreover, such treatments often provide less than satisfactory cure rates and patient tolerance. From a commercial standpoint, professional nail technicians and consumers of professional nail care products and services recognize that lifting and chipping of artificial (e.g. acrylic) nails is exacerbated by organic contaminants that grow at the interface of the natural nail and the artificial nail, or the artificial nail-coating interface. In addition, organic contaminants between the surface of the natural nail and a lacquer coating can cause lifting, chipping and reduced adhesion of lacquer coatings.

U.S. Pat. No. 4,957,730 discloses an antimycotic nail varnish. The nail varnish comprises, as anti-mycotic agents, certain 1-hydroxy-pyridones. However, the 1-hydroxy-pyridones have limited application because they are effective against mycotic organisms, not bacteria. Thus, in order to treat bacterial infections, an antibacterial agent would need to be somehow incorporated into these formulations. U.S. Pat. No. 5,487,776 discloses an anti-fungal nail lacquer and method for use thereof. The anti-fungal nail lacquer contains, as an anti-fungal agent, griseofulvin. However, griseofulvin, like the 1-hydroxy-pyridones of U.S. Pat. No. 4,957,730, is an anti-fungal agent and an additional antibacterial agent is required in order to treat bacterial infections. Furthermore, the disclosure provides that about 25 to 75 percent of the griseofulvin will generally be in solution, while the remaining 75 to 25 percent will generally be in colloidal suspension.

While alcohols are commonly used as solvents in nail lacquer compositions, prolonged contact between many antimicrobial agents can result in diminished activity of the antimicrobial agent. Clearly it would be advantageous, for esthetic reasons and for consistency in application, to have a true solution of an antimicrobial agent in a nail lacquer composition. It would also be advantageous if a nail lacquer composition were developed that provided both treatment and prophylaxis against a broad spectrum of microorganisms.

Thus, there remains a need for prophylaxis against polymicrobial infections of the nail plate, including continuous prophylaxis against acquired organic contamination after the application of a nail coating. It is also desirable to minimize or eliminate aldehyde and ketone solvents, particularly formaldehyde, in nail coatings. The present invention is directed to these, as well as other, important needs.

SUMMARY OF THE INVENTION

One aspect of the present invention provides an antimicrobial nail coating composition comprising an organic solvent, at least one film-forming polymer or resin, and an antimicrobial agent. Suitable antimicrobial agents for use in compositions of the present invention include, but are not limited to, antimicrobial quaternary amines and homologs thereof. Other similarly active, soluble antimicrobial agents known in the art can be used in compositions of the present invention.

Another aspect of the present invention is a method for treating microbial infections of the nail plate comprising applying to the nail area an antimicrobial nail coating composition comprising an organic solvent, at least one film-forming polymer or resin, and an antimicrobial agent.

A further aspect of the present invention is a method for preventing the spread of microbial infections of the nail plate comprising applying to the nail area an antimicrobial nail coating composition comprising an organic solvent, at least one film-forming polymer or resin, and an antimicrobial agent.

Additional features and embodiments of the present invention will become apparent to those skilled in the art in view of the ensuing disclosure and appended claims.

DETAILED DESCRIPTION OF THE INVENTION

It has been discovered that antimicrobial compositions containing antimicrobial agents, including quaternary amines and/or related homologs, can be advantageously incorporated within nail coatings to provide prophylaxis against susceptible organic contaminants. In connection with the present invention, it has further been surprisingly and unexpectedly found that antimicrobial agents having amine functionalities, such as quaternary amines, including benzalkonium chlorides, can form a solution in alcohol-containing solvents without becoming deactivated during storage.

The present invention provides antimicrobial compositions for nail coatings, and methods for manufacturing and using these compositions. The antimicrobial compositions of the present invention are intended for use on vertebrate nail plates, and present a useful means of immediate decontamination and extended prophylaxis against polymicrobial infections of the nail plate. The antimicrobial composition of the present invention may be formulated into basecoats and topcoats as defined herein. The compositions contain at least one antimicrobial agent, preferably a quaternary amine and/or at least one antimicrobially active homologue thereof.

The compositions of the present invention are intended as non-aqueous nail coatings, and generally contain typical components known in the art for use in non-aqueous nail coatings. As used herein, the term "non-aqueous" means containing less than 5 weight percent water, preferably less than 2 weight percent, and more preferably less than 1 weight percent. Quantities presented herein as "percent by weight" or "weight percent" refer to the percent of a particular component in a composition based on the total weight of the composition.

Antimicrobial agents that can be incorporated into the compositions of the present invention include agents that are commonly used for such applications and are chemically compatible with other components present in the nail coating compositions. Exemplary suitable antimicrobial agents for use in the present invention include quaternary amines, and phenol derivatives such as parachlorometaxylenol. Preferred antimicrobial agents are quaternary amines, and more preferred are benzalkonium chlorides (BAC), including antimicrobially active homologs thereof.

Antimicrobial agents used in the compositions of the present invention are advantageously employed at concentrations known to be antimicrobially effective on hard surfaces, e.g., agents commonly used in counter-top disinfectant formulations. Such antimicrobial agents are generally of low volatility, such that they are not lost by evaporation, and are retained in both the fluid and solid states of the compositions. For purposes of the present invention, the antimicrobial activity of the agents preferably remains substantially unchanged following transition of a nail coating composition from the fluid to the solid state, i.e., polymerization/solidification (see Table II, infra).

Antimicrobial agents are incorporated into the nail coating compositions of the present invention at a concentration of from about 0.05 percent to about 5 percent by weight, preferably from about 0.1 percent to about 2.5 percent by weight, and more preferably from about 0.3 percent to about 1 percent by weight. These quantities refer to the total amount of antimicrobial agent present in the composition, and can include one or more antimicrobial agents.

In preferred embodiments of the present invention, the antimicrobial nail coating compositions include a benzalkonium chloride (BAC) compound. The BAC can be in the form of a mixture of homologs, such as that defined by the United States Pharmacopaeia, or of an individual homolog.

Benzalkonium chlorides suitable for use in the compositions and methods of the present invention have the general formula (I)

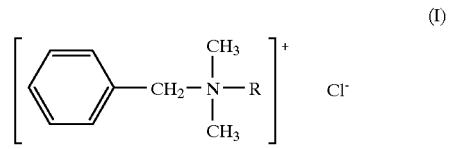

wherein R is an alkyl group having from 1 to 24 carbon atoms, commonly from 5 to 20 carbon atoms, preferably from 10 to 17 carbon atoms, more preferably from 10 to 15 carbon atoms, and even more preferably from 12 to 14 carbon atoms. In certain preferred embodiments, single homologs of benzalkonium chlorides, rather than mixtures thereof, are used as the antimicrobial agents in the compositions and methods of the present invention.

When BAC is used as the antimicrobial agent, or part thereof, in a composition of the present invention, the BAC homologs having the formula (I) will preferably constitute at least about 50 percent by weight, preferably at least about 75 percent by weight, more preferably at least about 90 percent by weight and most preferably at least about 95 percent by weight, of the antimicrobial agent. Most preferred for use in the compositions of the present invention are preferred BAC homologs containing alkyl groups (R) of 12, 13 or 14 carbon atoms.

Exemplary suitable BAC homologs, that may be used singly or in combination according to the present invention, include N,N-dimethyldecyl ammonium chloride, N,N-dimethyl-undecyl ammonium chloride, N,N-dimethyl-dodecyl-ammonium chloride, N,N-dimethyltridecylammonium chloride, N,N-dimethyl-tetradecylammonium chloride, N,N-dimethylpentadecylammonium chloride, N,N-dimethyl-hexadecylammonium chloride, and N,N-dimethylheptadecyl ammonium chloride.

Other antimicrobial agents that may be used in the compositions of the present invention, alone or in combination, include other antimicrobial quaternary amines and related compounds, such as, for example, monoalkyltrimethyl ammonium salts, dialkyl-ammonium salts, heteroaromatic ammonium salts, polysubstituted quaternary ammonium salts, bis-quaternary ammonium salts and polymeric quaternary ammonium salts.

Other antimicrobial agents, also referred to as germicidal agents, which may be used in compositions of the present invention alone or in combination, include phenols, including cresols and resorcinols. For example, parachlorometaxylenol is a suitable antimicrobial agent for use in the compositions of the present invention. Phenols, in concentrations of about 0.2, 1.0, and 1.3 percent by weight are bacteriostatic, bactericidal, and fungicidal, respectively. While it is not intended that the present invention be bound by any particular theory, it is believed that the germicidal action of phenols at these concentrations is effected through protein denaturation. The phenol-protein interaction is relatively weak, allowing the phenol molecule to penetrate deeply into the tissue. Thus, phenol can penetrate relatively dense, intact keratinous matrices, such as the stratum corneum or the nail plate. Several phenol derivatives are more potent than phenol itself, and the most important among these are the halogenated phenols and bis-phenols, the alkyl-substituted phenols and the resorcinols.

Examples of resorcinols useful in compositions of the present invention include resorcinol, hexylresorcinol, hexachlorophene, parabens, thymol, chlorothymol, parachlorometaxylenol, orthophenylphenol, p-tertiary butylphenol, p-tertiaryamylphenol, o-benzylphenyl-p-chlorophenol, parachlorophenol, camphorated parachlorophenol, tetrabromomethylphenol, and 2,6-dimethyl-4-chlorophenol. Resorcinols and other phenolic compounds may be employed in amounts from about 0.05 percent to about 5 percent by weight, preferably from about 0.1 percent to about 2.5 percent by weight and more preferably from about 0.3 percent to about 1 percent by weight.

Also suitable for use as germicides in the compositions of the present invention are antimicrobial biguanides. Biguanides are compatible with BAC formulations and are believed to function by causing cellular death by the disruption of the cell membrane of an infecting microorganism. Exemplary biguanides suitable for the present invention are chlorhexidine gluconate and its acetate derivative. These compounds may be employed in the present invention, singly or in combination, in amounts from about 0.05 percent to about 5 percent by weight, preferably from about 0.1 percent to about 4.5 percent by weight and more preferably from about 1.0 to about 4 percent by weight.

Another class of germicides suitable for use in the compositions of the present invention are antimicrobial furan derivatives. The presence of a nitro group at the five position of the 2-substituted furans confers antimicrobial activity to this class of compounds. An exemplary furan derivative suitable for use as a germicide according to the present invention is nitrofurazone. Furan derivatives may be incorporated into the present invention at concentrations of from about 0.05 percent to about 5.0 percent by weight, preferably from about 0.1 percent to about 3 percent by weight, and more preferably from about 0.5 percent to about 2 percent by weight.

Certain dyes exhibit antimicrobial activity and are suitable for use in the compositions of the present invention. Examples of suitable antimicrobial dyes include triphenylmethane hexamethylrosaniline chloride and tetramethylthionine chloride. Antimicrobial dyes may be incorporated into the present invention in concentrations of from about 0.01 percent to about 2 percent by weight, preferably from about 0.02 percent to about 1.5 percent by weight and more preferably from about 0.025 percent to about 1 percent by weight.

Other antimicrobial agents known in the art, that are compatible with the formulations disclosed herein that contain benzalkonium chlorides or phenol derivatives as antimicrobial agents, are suitable for use in the compositions of the present invention. Table I lists exemplary pharmacologic compounds that may be used in compositions of the present invention. In addition to specific examples of classes of antimicrobial agents in the categories discussed above, those skilled in the art will recognize that antimicrobial agents outside those categories, and that are compatible with other components in nail coating compositions, can be used in compositions of the present invention. Such active agents are effective against polymicrobial infections by various mechanisms of action. Suitable active agents are effective against, for example, infections caused by dermatophytic fungi, yeast, bacteria and molds. The active agents listed below, and/or others, can generally be incorporated into compositions of the present invention, singly or in combination, in quantities from about 0.05 percent to about 5 percent by weight, preferably from about 0.1 percent to about 2.5 percent by weight, and more preferably from about 0.3 percent to about 1 percent by weight, with the exact quantity determined in part by the activity and/or composition of the antimicrobial agent.

TABLE I

Antimicrobial Agents useful in compositions of the invention

| Generic | Product Name | Manufacturer |
|---|---|---|
| A. Agents used in treating dermatophyte infections | | |
| Amorolfine | Locery | Roche |
| Econazole-nitrate | Spectazole | Ortho |
| Naftifine | Naftin | Herbert Labs |
| Oxiconazole | Oxistat | Glaxo |
| Sulconazole | Exelderm | Westwood-Squibb |
| Terbinafine | Lamisil | Novartis |
| Tolnaftate | Tinactin | Schering-Plough |
| Undecylinic acid | Desinex | Pharmacraft |
| | Gordochrom | Gordon Labs |
| Griseofulvin | Fulvicin | Schering |
| Itraconazole | Sporonox | Janssen |
| Fluconazole | Diflucan | Pfeizer |
| B. Agent used in treating yeast infections | | |
| Nystatin | Mycostatin | Westwood-Squibb |
| C. Agents used in treating dermatophyte, yeast and bacterial infections | | |
| Ciclopiroxolamine | Loprox | Hoechst-Roussel |
| Clotrimazole | Lotrimin | Schering-Plough |
| Econazole-nitrate | Spectazole | Ortho |
| Haloprogin | Halotex | Westwood-Squibb |
| Miconazole | Micatin/ | Ortho |
| | Fungoid Tincture | Pedinol |
| Quaternium 12 | Mone | Kenlor Industries |
| D. Agents used in treating nondermatophyte (saprophyte) opportunistic infections | | |
| Amphotericin B | Fungizone | Bristol-Myers Squibb |
| Ketoconazole | Nizoral | Janssen |
| BAC | Mycocide NS | Woodward Labs |
| Fluconazole | Diflucan | Roerig-Pfizer |
| Itraconazole | Sporanox | Janssen |
| E. Agents used in treating deep (systemic) mycotic infections | | |
| Flucytosine | Ancobon | Roche |
| F. Agents used in treating actinomycetes infections | | |
| Amikacin | Amikin | Apothecon |
| Ampicillin | Omnipen | Wyeth-Ayerst |
| | Polycillin | Apothecon |
| | Principen | Apothecon |
| Penicillin-G | Bicillin | Wyeth-Ayerst |
| | Wycillin | Wyeth-Ayerst |
| Tetracycline | Doxycycline | Laderle |
| Trimethoprim | Bactrim | Roche |
| Sulfamethoxazole | Septra | Glaxo-Wellcome |

To provide an acceptably functional nail coating, the antimicrobial compositions of the present invention preferably employ one or more of the following components, either alone or in combination: film-forming polymers, resins, plasticizers, solvents, diluents, colors and/or pigments, ultraviolet light-absorbing agents, suspension and viscosity regulating, vitamins, proteins and/or growth promoters, drying accelerators, hardening accelerators, lipids and vitamins.

Film-forming polymers can add thickness and gloss to a nail preparation following polymerization. For use in compositions of the present invention, the film formed by polymerization should demonstrate good adhesion characteristics, and be flexible enough to avoid significant chipping and cracking, as demonstrated by the seven day durability test described by Shansky [Shansky, A. *Drug Cosmet. Ind.* 123(5):46, 1978.]. By "good adhesion" is meant that a coating will display little lifting and/or chipping, preferably substantially no lifting and/or chipping, for about 3 to about 5 days after application to a natural nail and for about 7 to about 10 days after application to an acrylic nail. Such film-forming polymers are well known to those skilled in the art and include such polymers as are generally employed in photoreactions. Types of film-forming polymers suitable for use in compositions of the present invention include cellulose derivatives such as cellulose esters and nitrocellulose, and acrylic polymers. Cellulose derivatives suitable as film-forming agents are listed in U.S. Pat. No. 5,516,509, the disclosure of which is hereby incorporated herein by reference. Specific examples of suitable film-forming polymers include poly(methyl methacrylate), poly(ethyl methacrylate), poly(butylmethacrylate), cellulose acetate, cellulose acetate propionate, and cellulose acetate butyrate. In addition to film-forming polymers, the compositions of the present invention can include monomers that form a film upon photopolymerization. Suitable monomers include acrylic monomers such as methylmethacrylate, ethylmethacrylate, and butylmethacrylate. The amount of film-forming polymer, if used, is from about 5 to about 65 percent by weight, preferably from about 7 percent to about 50 percent by weight and more preferably from about 10 percent to about 30 percent by weight, based on the total weight of the composition and including the weight of the monomers.

Resins are typically added to nail coatings to enhance gloss, hardness and adhesion and decrease susceptibility to detergents. [Wilkinson, J. B., and Moore, R. J., Eds. The Nails. Chapter 22 in Harry's Cosmeticology, 7th Edition, pp 369–393, Chemical Publishing Company, Inc. New York, N.Y. 1982]. Such resins are well known to those skilled in the art, and examples of compatible resins for use in the compositions of the present invention include shellac, pontianak, and synthetic resins such as acrylic copolymers, polyvinyl acetate, butyrates and arylsulfonamide-formaldehyde resins. Other resins that are compatible with the present formulation are melamine formaldehyde, urea formaldehyde, the styrene alkyds and the family of polyester resins and rosin based resins. If desired, nylon solids may be added to formulations for use according to the invention to accelerate the drying of the resin, and to enhance the film-forming characteristics. Resins are optional components in the compositions of the present invention, and certain film-forming polymers, such as nitrocellulose, can provide satisfactory adhesion characteristics so that resins are not needed. Suitable concentrations of resins for use in the compositions of the present invention are from about 1 percent to about 80 percent by weight, preferably from about 3 percent to about 25 percent by weight and more preferably from about 3.5 percent to about 10 percent by weight. Also preferably, compositions of the present invention containing resins, when dry, have a resin solids content of from about 20 percent to about 40 percent by weight.

Plasticizers can be used in nail formulations to decrease brittleness and chipping. Such plasticizers are well known to those skilled in the art, and exemplary types of suitable plasticizers for use in compositions of the present invention include organic phthalates, adipates and phosphates. Particular plasticizers suitable for use in the compositions of the present invention include sucrose diacetate hexaisobutyrate, glyceryl tribenzoate, tricresyl phosphate, dibutyl phthalate, butyl benzyl phthalate, butyl phthalyl, butyl glycolate, dioctyl phthalate, triphenyl phosphate, dibutoxy ethyl phthalate, camphor, castor oil, benzyl benzoate, tributyl phosphate, butyl acetate ricenoleate, butyl stearate, triethyl citrate, dibutyl tartrate, diamyl phthalate, phosphoinositides and lysophosphatides. The amount of plasticizer, if used, is from about 0.5 percent to about 30 percent by weight, preferably of from about 1 percent to about 20 percent by weight, and more preferably from about 2 to about 10 percent by weight.

One or more solvents can be used to facilitate suspension of solid components in nail coating formulations ("The Nails", supra, pp 369–393). The solvents are preferably non-aqueous. Such solvents are well known to those skilled in the art, and exemplary types of solvents compatible with the formulations of the present invention include alkanes, alkanols, ketones, esters including acetates, amides, ethers, alcohols, glycol-ethers and nitroparaffins. Specific examples of these types of solvents include ethyl ether, petroleum ether, methyl acetate, acetone, cyclohexane, ethyl acetate, methyl ethyl ketone, carbon tetrachloride, ethyl alcohol, n-butyl acetate, isobutyl acetate, amyl acetate, xylol, isopropyl alcohol, butyl alcohol, diethylene glycol monomethylether, diethylene glycol monoethylene ether and ethyl lactate. Also suitable as solvents are acyclic aliphatic and cycloaliphatic compounds. As noted, aldehydes and ketones are not preferred for use as solvents in the compositions of the present invention. The amount of solvent present in the nail coating compositions can be from about 10 percent to about 80 percent by weight, preferably from about 15 percent to about 60 percent by weight, and more preferably from about 38 percent to about 50 percent by weight. When alcohols are used as solvents, it is preferred that the solvent include one or more alcohols in combination with one or more non-alcoholic solvents. For example, a suitable solvent can advantageously comprise one or more alcohols, especially isopropyl alcohol, and one or more esters, such as butyl acetate and/or ethyl acetate. Generally, it is preferred that the amount of alcohol be less than about 20 percent by weight, more preferably less than about 15 percent by weight, based on the total weight of the composition.

Furthermore, it will be appreciated by those skilled in the art that certain solvents can also function as plasticizers, thereby eliminating the need to use a separate plasticizer component. Whether or not a plasticizer is needed in the presence of a given quantity and type of solvent can readily be determined by one skilled in the art with minimal experimentation. Solvents that can also function as plasticizers include, but are not limited to, methyl acetate, ethyl acetate, n-butyl acetate, methyl ether, petroleum ether, cyclohexane, methyl-ethyl ketone, carbon tetrachloride, ethyl alcohol, isopropyl alcohol, n-butyl alcohol, diethylene glycol monoethyl ether, diethyleneglycol monomethyl ether, and xylol. Other compounds suitable as solvents will be apparent to those skilled in the art.

If desired, one or more diluents can be used to improve stabilization of viscosity, and to control the overall cost of the formulation. Examples of compounds that are useful as diluents in formulations of the present invention include alcohols, aromatic hydrocarbons and aliphatic hydrocarbons. Specific examples of suitable diluents include ethanol, butanol, isopropanol, toluene and xylene. Suitable concentration ranges of diluents for use in compositions of the present invention are from about 1 percent to about 80 percent by weight. preferably from about 5 percent to about 60 percent by weight and more preferably from about 10 percent to about 50 percent by weight. As noted, formulations of the present invention preferably exclude toluene and formaldehyde. However, formulations containing toluene and/or formaldehyde are within the scope of the present invention. If present, the amount of formaldehyde in compositions of the present invention is preferably from 0.1 percent by weight to about 10 percent by weight, preferably from about 0.5 percent to about 7.5 percent by weight, and more preferably from about 2 percent to about 5 percent by weight. Examples of toluene-free and formaldehyde-free embodiments of the present invention are provided below.

Pigments and other coloring agents can be used for enhancement of the esthetic qualities of embodiments of the present invention. Colors and pigments useful in nail coating compositions are well known to those skilled in the art. Compiled lists of such components are available from the United States Food and Drug Administration. Examples of suitable coloring agents for use in compositions of the present invention include the insoluble lakes and colored polymeric material, opacity regulating agents such as titanium dioxide, aluminum silicate, tinting agents such as iron oxide, and pearlescent agents such as guanine bismuth oxychloride. Specific examples of pigments compatible with compositions of the present invention include D&C Red 6, D&C Red 30, D&C Red 36, D&C Red 9, D&C Red 7, FD&C Yellow 5, and FD&C Yellow 6.

The amount of pigment used in a nail coating composition such as a colored lacquer can vary, but generally does not exceed about 15 percent by weight, based on the total weight of the composition. For improved wear resistance, the pigment concentration in nail coatings should not be lower than about 3 percent by weight. In compositions of the present invention, the amount of pigments and/or other coloring agents, if the coloring agents are pearlescent, is preferably from about 0.05 percent to about 6 percent by weight, more preferably from about 0.1 percent to about 5.5 percent by weight, and still more preferably from about 0.5 percent to about 5 percent by weight. Suitable amounts of pearlescent components range from about 0.5 percent to about 15 percent by weight, preferably from about 1 percent to about 12.5 percent by weight and more preferably from about 2 percent to about 11 percent by weight.

If desired, compositions of the present invention can be prepared without pigments or coloring agents. Such colorless antimicrobial nail compositions are suitable for use as, for example, basecoats or topcoats when used with pigmented nail coatings, or can be used alone.

Ultraviolet (UV) light-absorbing agents can be used in the compositions of the present invention to inhibit photolysis of susceptible chemical compounds and thereby minimize concomitant discoloration of the finished formulation (Wilkinson, J. B., and Moore, R. J., Eds. "The Nails", supra). Any suitable UV blocker, or combination of blockers, commonly used in non-aqueous nail coating formulations can be used in the compositions of the present invention. Specific examples include benzophenone and derivatives thereof, and FD&C and D&C colors known to absorb UV radiation. The amount of UV absorbing agent in compositions of the present invention can range from about 0.01 percent to about 2 percent by weight, preferably from about 0.05 percent to about 1 percent by weight, and more preferably from about 0.06 to about 0.5 percent by weight.

Suspension and/or viscosity regulating agents can be used to facilitate the ease of application of the compositions of the present invention, and to improve uniformity of flow. Appropriate suspension agents include dimethyl dioctadecyl ammonium bentonite, benzyl dimethyl hydrogenated tallow ammonium montmorillonite, and dimethyl dioctadecyl ammonium hectorite. Appropriate viscosity regulating agents that may be used include fused silica and pulverized glass. The amount of suspension/viscosity regulating agents used can be from about 0.05 percent to about 10 percent by weight, preferably from about 0.2 percent by weight to about 7 percent by weight, and more preferably from about 1 percent to about 4 percent by weight. If desired, in addition to or instead of the above-mentioned compounds, the viscosity may be further regulated through the addition of polyvalent acids, such as orthophosphoric acid, in an amount from about 0.05 percent to about 7 percent by weight, preferably from about 0.25 percent to about 6 percent by weight and more preferably from about 0.5 percent to about 2 percent by weight.

If desired, the compositions of the present invention can include vitamins, proteins and growth promoters, either alone or in combination. Exemplary suitable vitamins include lipid soluble vitamins, such as the tocopherols, phytonadione, menaquinone, menadione, retinol, 3-dehydroretinol; and various amphiphylic water soluble vitamins, such as cholecalciferol. Other optional components include amphiphylic amino acids and peptides compatible with the compositions of the present invention. Also suitable are agents that are known to promote the growth of fibroblasts and keratinocytes and are compatible with the compositions of the present invention, such as the phosphatidates, and lyso- derivatives such as lysophosphatidic acid. Vitamins, proteins and growth promoters, as a group, can be present in the compositions of the present invention in amounts from about 0.001 percent to about 5 percent by weight, preferably from about 0.01 percent to about 3 percent by weight, and more preferably from about 0.05 percent to about 2 percent by weight.

Drying accelerators are commonly used to speed up the drying process of nail coating formulations, as discussed in U.S. Pat. No. 5,045,309. Hydrocarbons that are compatible with the present invention, and that can be used to decrease the overall drying time of nail coating compositions according to the invention include the halogenated hydrocarbons, specifically trichlorotrifluoroethane. Suitable concentrations of the optional drying accelerators are from about 10 percent to about 50 percent by weight, preferably from about 2 percent to about 40 percent by weight, and more preferably from about 30 percent to about 37 percent by weight.

If desired, drying and hardening accelerators can be used to accelerate the process of hardening agents used in nail coating formulations. Hardening accelerators suitable for use in the compositions of the present invention include ultraviolet light-activated curing compositions such as those described in U.S. Pat, Nos. 5,118,495 and 5,516,509, and heat-activated curing compositions. Light-activated accelerators generally contain one or more photoinitiators such as alkyl- and heterocyclic-phenyl ketones, and one or more photoreactive monomers, such as methacrylic acid esters including methyl methacrylate. Photoinitiators can be used in amounts from about 0.05 percent to about 10 percent by weight, preferably from about 2.5 percent to about 8 percent by weight, and more preferably from about 3 percent to about 5 percent by weight. Photoreactive monomers can be used in amounts from about 40 percent to about 80 percent by weight, preferably from about 45 percent to about 60 percent by weight, and more preferably from about 50 percent to about 55 percent by weight. Examples of components used in heat activated curing compositions that can be included in compositions of the present invention include methyl ethyl ketone, methacrylate ester, and hydroxyhydrocinnamate ester, alone or in conjunction with aliphatic esters. Concentrations of heat-activated curing compositions for the present invention can range from about 0.05 percent to about 10 percent by weight, preferably from about 2.5 percent to about 8 percent by weight, and more preferably from about 3 percent to about 5 percent by weight.

Lipids can be included in the compositions of the present invention. Lipids are important to the functioning of the nail plate as a barrier. However, lipids can be stripped from the nail by organic solvents normally used in nail care preparations. It is known that lipids can be applied to dried, hardened nail coatings and can enhance the shine of the coatings. However, it has been discovered in connection with the present invention that lipids can be incorporated directly into nail coating compositions. The presence of lipids in nail coating compositions can help to ameliorate the depletion of lipids from the nail. Furthermore, while it is not intended that the present invention be bound by any particular theory, it is believed that lipids incorporated into nail coating compositions can diffuse from the interior of the nail coating to the air/coating surface and/or the nail/coating surface over time, thus continuing to enhance shine and provide benefits to the nail.

Generally, any lipids compatible with the compositions of the present invention can be used. Suitable lipids are well known to those skilled in the art. Exemplary suitable lipids for use in the compositions of the present invention include phospholipids, such as phosphatidylcholine, phosphatidylinositol, phosphatidyl serine and phosphatidylethanolamine, lysophospholipids such as lysophosphatidic acid, fatty acids, cholesterol, cholesterol esters, waxes, squalene, triglycerides and sphingolipids. In particular, suitable sphingolipids include ceramide sphingosine, sphingomyelin, and glycolipids including cerebrosides. If present, the concentration of lipids in compositions of the present invention can be from about 0.001 weight percent to about 2 weight percent, preferably from about 0.001 to about 1 weight percent, and more preferably from about 0.01 to about 0.5 weight percent. If desired, oils can be included in the compositions of the present invention. For example, tea tree oil is compatible with the compositions of the invention and can be used therein. Also suitable are one or more individual components of tea tree oil, such as terpinen-4-ol, alpha terpineol, alpha pinene, and combinations thereof with or without tea tree oil. Such components can be derived from natural sources, or can be synthesized using methods known to those skilled in the art. Oils can be present in an amount from about 0.01 weight percent to about 20 weight percent, preferably from about 0.05 weight percent to about 5 weight percent, and even more preferably from about 0.1 weight percent to about 3 weight percent.

Lipid and/or water soluble vitamins can also optionally be included in the nail coating compositions of the present invention. These vitamins are nutrients needed by the cells of the nail matrix that are involved in the production of keratin and the formation of new nail plate tissue. In particular, lipid soluble vitamins are particularly compatible with the nail coating compositions of the present invention. Suitable lipid soluble vitamins for use in the nail coating compositions include vitamins A, E, K, H and D. Particularly useful are vitamin D, and analogs or precursors thereof, which play a significant role in keratinization of the nail matrix cells. Exemplary suitable vitamin D precursors include ergosterol, 7-dehydrocholesterol, calciferol, cholecalciferol, calcifediol, calcitrol, α-hydroxycholecalciferol and dihydrotachysterol. Vitamins can be present in the compositions of the present invention in concentrations of from about 0.0001 to about 2 weight percent, preferably from about 0.001 to about 1 weight percent, and more preferably from about 0.01 to about 0.5 weight percent.

EXAMPLES

The following examples are merely illustrative of the present invention and should not be considered limiting of the scope of the invention in any way. These examples and equivalents thereof will become more apparent to those skilled in the art in light of the present disclosure and the accompanying claims.

1. Preparation of nail coating compositions

Nail coating compositions were prepared to demonstrate the effectiveness of an incorporated antimicrobial agent. Composition 1, containing as an antimicrobial agent a USP grade BAC, was compared to Composition 2, which did not contain an antimicrobial agent. The compositions were prepared according to the following formulations:

| Composition 1 | |
| --- | --- |
| Component | Percent (by weight) |
| Butyl acetate | 30.0 |
| N-amyl acetate | 30.0 |
| Dibutylphthalate | 3.0 |
| Santolite resin | 5.00 |
| Nitrocellulose | 15.0 |
| Isopropyl alcohol | 16.0 |
| Benzalkonium chloride (USP grade) | 1.0 |

| Composition 2 | |
| --- | --- |
| Component | Percent (wt) |
| Butyl acetate | 30.0 |
| N-amyl acetate | 30.0 |
| Dibutylphthalate | 3.0 |
| Santolite resin | 5.0 |
| Nitrocellulose | 15.0 |
| Isopropyl alcohol | 17.0 |

The components of each composition were mixed together at room temperature in the following manner. Liquid components were combined, into which nitrocellulose was then dissolved. Benzalkonium chloride was added and the mixture was stirred until visibly free of any undissolved solids. Upon application to nails, the solution dried in less than 2 minutes to a flexible, non-brittle coating of acceptable handling and esthetic qualities for a basecoat, with durability consistent with Shansky's testing method (Shansky, A. *Drug Cosmet. Ind.* 123(5):46(1978)).

The dried coating was evaluated according to an approved surface carrier disinfection test (Official Methods of Analysis of the Association of Official Analytical Chemists protocol 991.47: Hard surface carrier test method). Cultures of a selected test organism were grown for 24 hours at room temperature in the appropriate growth medium to a density of approximately McFarland standard #10. Sterile glass cylinders (Belco Cat. #2090-S0012) served as carriers. The carriers were coated with the test Composition 1 or the control Composition 2. They were then allowed to dry at room temperature, and subsequently submerged in 5 ml of the stock culture, and allowed to remain there for 15 minutes.

Carriers treated with Composition 1 (BAC), carriers treated with Composition 2 (no agent) and control carriers (untreated) were aseptically transferred to sterile, dry Whatman #1 filter paper, and excess droplets of inoculation medium were removed. The carriers were allowed to dry at 37° C. for 40 minutes and then aseptically transferred to 5 ml of trypsin soy broth. They were subsequently sonicated for 10 minutes in a water bath at 25° C. Tubes containing the sonicated carriers were vortexed, and a portion of the medium was plated onto Trypsin Soy agar plates, and incubated overnight at 37° C. Bacterial growth was assessed by counting colonies. The results indicated that treatment with Composition 1 containing the formulation with BAC caused a significantly greater reduction of bacterial growth than did treatment with the non-antimicrobial control Composition 2, as compared with bacterial growth on untreated carriers. Testing results are shown in Table II.

TABLE II

Results of antimicrobial quality testing of nail coating prepared according to Example 1.

| ORGANISM | CONDITION | COLONIES REMAINING |
|---|---|---|
| Candida albicans | Control | 1192 |
| ATCC 10231 | Composition 2 | 66 |
| | Composition 1 (BAC) | 20 |
| Enterococcus fecalis | Control | >10,000 |
| ATCC 49452 | Composition 2 | >10,000 |
| | Composition 1 (BAC) | 442 |
| Eschericia coli | Control | >1000 |
| ATCC 11229 | Composition 2 | 72 |
| | Composition 1 (BAC) | 0 |
| Pseudimonas | Control | >10,000 |
| aeruginosa | Composition 2 | 1780 |
| ATCC 9027 | Composition 1 (BAC) | 0 |
| Salmonella cholerasuis | Control | >1000 |
| enteriditis | Composition 2 | >1000 |
| ATCC 13076 | Composition 1 (BAC) | 0 |
| Salmonella cholerasuis | Control | >1000 |
| typhimurium | Composition 2 | >1000 |
| ATCC 19585 | Composition 1 (BAC) | 0 |
| Staphylococcus aureus | Control | >10,000 |
| ATCC 6538 | Composition 2 | >10,000 |
| | Composition 1 (BAC) | 160 |

Example 2

Three nail coating compositions were formulated as follows:

Solution 1 (BAC)

| Component | Percent (by weight) |
|---|---|
| Toluene | 37.39 |
| Ethyl acetate | 32.21 |
| Ethyl alcohol | 2.00 |
| Dibutyl phthalate | 3.40 |
| Santolite resin | 10.0 |
| Nitrocellulose | 10.0 |
| BAC (USP) | 1.0 |
| Isopropyl alcohol | 4.00 |

Solution 2 (PCMX)

| Component | Percent (wt) |
|---|---|
| Toluene | 37.39 |
| Ethyl acetate | 32.21 |
| Ethyl alcohol | 2.00 |
| Dibutyl phthalate | 3.40 |
| Santolite resin | 10.0 |
| Nitrocellulose | 10.0 |
| Parachlorometaxylenol (PCMX) | 1.0 |
| Isopropyl alcohol | 4.00 |

Solution 3 (Vehicle)

| Component | Percent (wt) |
|---|---|
| Toluene | 37.39 |
| Ethyl acetate | 32.21 |
| Ethyl alcohol | 2.00 |
| Dibutyl phthalate | 3.40 |
| Santolite resin | 10.0 |
| Nitrocellulose | 10.0 |
| Isopropyl alcohol | 5.00 |

The above formulations were prepared as in Example 2, and formed a flexible, non-brittle coating of acceptable handling and aesthetic qualities for a basecoat, topcoat or nail lacquer. Furthermore, when the polymerized coating was tested according to the approved surface carrier disinfection test (see above) the preparation caused a significantly greater reduction of bacteria than did a non-antimicrobial, vehicle control. Solution 1, containing BAC (USP) demonstrated greater antimicrobial efficacy than did the solution containing the other test antimicrobial, PCMX (Table III).

It should be noted that PCMX is a phenol derivative and BAC is a quaternary amine, and phenol derivatives are expected to be more compatible with the generally non-aqueous, non polar environment of the current invention. However, it is important to note that BAC, which would be expected to be more compatible with an aqueous, polar environment, is also stable in the formulation prepared according to the present invention, illustrating the wide range of chemical properties tolerated by the compositions of the present invention, and the compatibility of the compositions with a large number of antimicrobial active agents.

TABLE III

Comparative antimicrobial test of BAC and PCMX.

| Organism | Condition | Bacteria remaining |
|---|---|---|
| Serratia marcescens | Control | >1000 |
| ATCC 14756 | Vehicle (Soln 3) | >1000 |
| | PCMX Basecoat (Soln 2) | 16 |
| | BAC Basecoat (Soln 1) | 0 |

Example 3 (Prophetic)

Formulations containing tea tree oil can be made with or without toluene.

Toluene-containing formulation with tea tree oil

| Toluene | 45% |
|---|---|
| Ethyl acetate | 10% |
| Butyl acetate | 10% |
| Nitrocellulose | 15% |
| Adhesive resin | 10% |
| Isopropanol | 7% |
| Tea Tree Oil | 3% |

TABLE III-continued

Toluene-free formulation with tea tree oil

| | |
|---|---|
| Ethyl acetate | 25% |
| Butyl acetate | 20% |
| Isopropanol | 25% |
| Nitrocellulose | 15% |
| Adhesive resin | 10% |
| Tea Tree Oil | 5% |

What is claimed is:

1. A method for treating a microbial infection of the nail plate comprising applying to the nail a non-aqueous antimicrobial nail coating composition comprising:
   (a) from about 5 percent to about 65 percent by weight of a film-forming polymer;
   (b) from about 10 percent to about 80 percent by weight of an organic solvent; and
   (c) from about 0.05 percent to about 5 percent by weight of an antimicrobial agent, wherein
   said antimicrobial agent comprises solubilized benzalkonium chloride;
   wherein the benzalkonium chloride
   (1) is capable of leaching from said nail coating composition following transition of the nail coating from a liquid to a solid state following application;
   (2) retains its antimicrobial activity following (1); and
   (3) is not inactivated by isopropyl alcohol during storage,
   wherein all weight percentages are based on the total weight of the nail coating composition.

2. The method of claim 1 wherein said antimicrobial agent comprises benzalkonium chloride having the formula

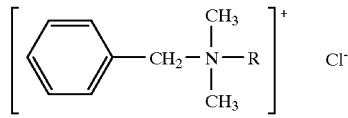

wherein R is an alkyl group of from 1 to 24 carbon atoms.

3. The method of claim 1 wherein R is an alkyl group of from 10 to 17 carbon atoms.

4. The method of claim 1 wherein said nail coating composition further comprises from about 1 percent to about 80 percent by weight of a resin.

5. A method for treating a microbial infection of the nail plate comprising applying to the nail a non-aqueous antimicrobial nail coating composition comprising:
   (a) from about 1 percent to about 80 percent by weight of a resin;
   (b) from about 10 percent to about 80 percent by weight of an organic solvent; and
   (c) from about 0.05 percent to about 5 percent by weight of an antimicrobial agent, wherein said antimicrobial agent comprises solubilized benzalkonium chloride;

wherein the benzalkonium cholride (1) is capable of leaching from said nail coating composition following transition of the nail coating from a liquid to a solid state following application;
   (2) retains its antimicrobial activity following (1); and
   (3) is not inactivated by isopropyl alcohol during storage, wherein all weight percentages are based on the total weight of the nail coating composition.

6. The method of claim 5 wherein said antimicrobial agent comprises benzalkonium chloride having the formula

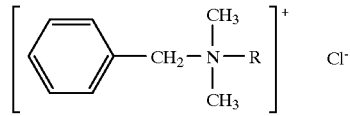

wherein R is an alkyl group of from 1 to 24 carbon atoms.

7. The method of claim 6 wherein R is an alkyl group of from 10 to 17 carbon atoms.

* * * * *